US012708184B2

(12) United States Patent
Allen et al.

(10) Patent No.: US 12,708,184 B2
(45) Date of Patent: Aug. 18, 2026

(54) RING WITH ADAPTIVE FORCE REGION

(71) Applicant: HAPPY HEALTH INC., Austin, TX (US)

(72) Inventors: Dan Allen, Springville, UT (US); David E. Clift-Reaves, Austin, TX (US)

(73) Assignee: HAPPY HEALTH INC., Austin, TX (US)

( * ) Notice: Subject to any disclaimer, the term of this patent is extended or adjusted under 35 U.S.C. 154(b) by 684 days.

(21) Appl. No.: 18/018,374

(22) PCT Filed: Jul. 28, 2021

(86) PCT No.: PCT/US2021/043486
§ 371 (c)(1),
(2) Date: Jan. 27, 2023

(87) PCT Pub. No.: WO2022/026567
PCT Pub. Date: Feb. 3, 2022

(65) Prior Publication Data

US 2023/0284754 A1 Sep. 14, 2023

Related U.S. Application Data

(60) Provisional application No. 63/057,820, filed on Jul. 28, 2020.

(51) Int. Cl.

| | |
|---|---|
| ***A44C 9/00*** | (2006.01) |
| ***A44C 9/02*** | (2006.01) |
| ***A61B 5/00*** | (2006.01) |
| ***G06F 1/16*** | (2006.01) |

(52) U.S. Cl.
CPC .............. *A44C 9/0053* (2013.01); *A44C 9/02* (2013.01); *A61B 5/6826* (2013.01); *A61B 5/6843* (2013.01); *G06F 1/163* (2013.01)

(58) Field of Classification Search
CPC . A61B 5/0205; A61B 5/1455; A61B 5/14551; A61B 5/14552; A61B 5/14532; A61B 5/6826; A61B 5/6843; A61B 5/6822; A61B 5/6814; A61B 5/6824; A61B 5/6828; A44C 9/02
See application file for complete search history.

(56) References Cited

U.S. PATENT DOCUMENTS

| | | | | |
|---|---|---|---|---|
| 3,557,571 A | 1/1971 | De Santo | | |
| 9,711,060 B1 | 7/2017 | Lusted et al. | | |
| 2002/0169381 A1* | 11/2002 | Asada | ................ | A61B 5/14552 600/500 |

(Continued)

FOREIGN PATENT DOCUMENTS

| | | |
|---|---|---|
| CN | 205214428 U | 5/2016 |

OTHER PUBLICATIONS

International Search Report and Written Opinion for International application No. PCT/US2021/043486, mailed Oct. 27, 2021, 2021, 11 pages.

(Continued)

*Primary Examiner* — Chu Chuan Liu
(74) *Attorney, Agent, or Firm* — Polsinelli PC

(57) ABSTRACT

A ring includes a toroid having an inner portion. An adaptive force region is extending from the inner portion. The adaptive force region is operable to exhibit non-Hookean deformation.

20 Claims, 13 Drawing Sheets

(56) References Cited

U.S. PATENT DOCUMENTS

| | | | | |
|---|---|---|---|---|
| 2008/0163646 | A1* | 7/2008 | Czajka ..................... | A44C 9/02<br>63/15.6 |
| 2011/0210931 | A1 | 9/2011 | Shai | |
| 2013/0226015 | A1* | 8/2013 | Lam ................... | A61B 5/02241<br>600/499 |
| 2014/0375465 | A1 | 12/2014 | Fenuccio et al. | |
| 2016/0361016 | A1 | 12/2016 | Tverskoy | |
| 2017/0083115 | A1 | 3/2017 | Speck | |
| 2019/0125042 | A1* | 5/2019 | Bassan ................... | A44C 17/02 |
| 2019/0187835 | A1 | 6/2019 | Griffin | |
| 2019/0298186 | A1 | 10/2019 | Fine et al. | |
| 2020/0000345 | A1* | 1/2020 | Connor .............. | A61B 5/14551 |

OTHER PUBLICATIONS

Extended European Search Report for EP Application No. 21851342.2, dated Jul. 5, 2024, 7 pages.

Examination Report for EP Application No. 21851342.2, dated May 27, 2025, 6 pages.

* cited by examiner

RING WITH ADAPTIVE FORCE REGION

CROSS-REFERENCE TO RELATED APPLICATIONS

The application is a national stage application of International Application No. PCT/US2021/043486, which was filed on Jul. 28, 2021, which claims benefit and priority to U.S. provisional patent application No. 63/057,820, filed Jul. 28, 2020, title "Ring With Adaptive Force Region", the disclosure of which is hereby incorporated by reference in their entirety.

FIELD

The present disclosure generally relates to a non-invasive device for monitoring biological parameters of a user. In particular, the present disclosure relates to a ring for monitoring the biological parameters of a user via a biosensor having one or more deformable structures to maintain the positioning of the body part disposed in the ring.

BACKGROUND

Numerous monitoring devices are currently available in the market configured to track various aspects of a user's biological and physiological parameters. Such devices can be capable of tracking factors such as a user's heart rate, physical activity throughout a defined period, steps taken throughout a defined period, wellness, and the like. Such devices can be wearable and in some examples can be integrated into garments, hats, wristbands, watches, socks, shoes, eyeglasses, headphones, smartphones, and other wearable items. Such devices can be configured to perform health and wellness tracking.

BRIEF DESCRIPTION OF THE DRAWINGS

Implementations of the present technology will now be described, by way of example only, with reference to the attached figures, wherein.

DETAILED DESCRIPTION

Figure 1:
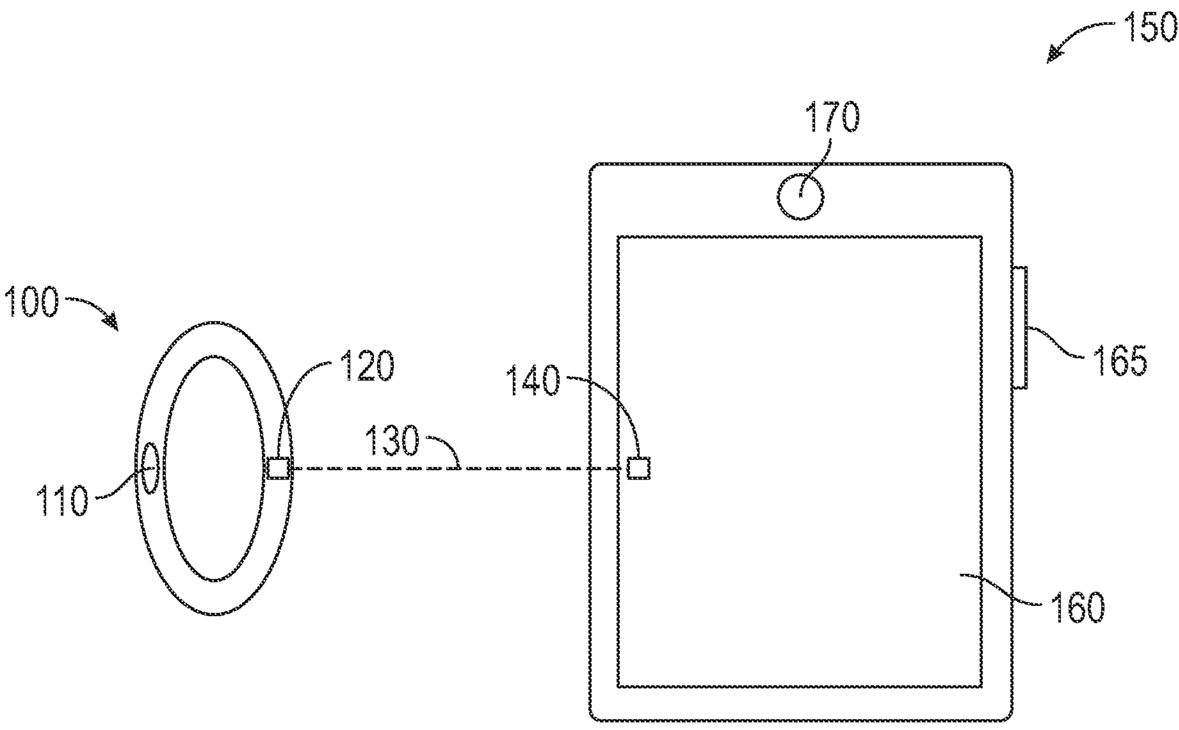
FIG. 1 is a diagrammatic view of a ring and an output device, according to at least one instance of the present disclosure.

Examples and various features and advantageous details thereof are explained more fully with reference to the exemplary, and therefore non-limiting, examples illustrated in the accompanying drawings and detailed in the following description. Descriptions of known starting materials and processes can be omitted so as not to unnecessarily obscure the disclosure in detail. It should be understood, however, that the detailed description and the specific examples, while indicating the preferred examples, are given by way of illustration only and not by way of limitation. Various substitutions, modifications, additions and/or rearrangements within the spirit and/or scope of the underlying inventive concept will become apparent to those skilled in the art from this disclosure.

I. TERMINOLOGY

As used herein, the terms "comprises," "comprising," "includes," "including," "has," "having" or any other variation thereof, are intended to cover a non-exclusive inclusion. For example, a process, product, article, or apparatus that comprises a list of elements is not necessarily limited only those elements but can include other elements not expressly listed or inherent to such process, process, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Additionally, any examples or illustrations given herein are not to be regarded in any way as restrictions on, limits to, or express definitions of, any term or terms with which they are utilized. Instead, these examples or illustrations are to be regarded as being described with respect to one particular example and as illustrative only. Those of ordinary skill in the art will appreciate that any term or terms with which these examples or illustrations are utilized encompass other examples as well as implementations and adaptations thereof which can or cannot be given therewith or elsewhere in the specification and all such examples are intended to be included within the scope of that term or terms. Language designating such non-limiting examples and illustrations includes, but is not limited to: "for example," "for instance," "e.g.," "In some examples," and the like.

Although the terms first, second, etc. can be used herein to describe various elements, components, regions, layers and/or sections, these elements, components, regions, layers and/or sections should not be limited by these terms. These terms are only used to distinguish one element, component, region, layer or section from another. Thus, a first element, component, region, layer or section discussed below could be termed a second element, component, region, layer or section without departing from the teachings of the present inventive concept.

The term "deformation" or "deform" or any other variation thereof as used herein refers to a change in shape or distortion of shape, for example through the application of a force.

The term "Hookean" as used herein (including, but not limited to, terms such as Hookean response, Hookean material, and the like) refers to objects subject to Hooke's law, or which follow's Hooke's law. Materials which are subject to Hooke's law can include materials which are linearly elastic. Correspondingly, the term "non-Hookean" as used herein (including, but not limited to terms such as non-Hookean response, non-Hookean material, and the like) refer to objects that are not subject to Hooke's law. For example, a non-Hookean material can include materials which show elasticity that is stress and/or force dependent, sensitive to temperature changes, and/or loading rate. Non-Hookean materials can have a force constant which can decrease with deformation.

II. GENERAL ARCHITECTURE

Wearable biometric measurements can have artifacts arising from motion between the sensor and the wearer. While a more tightly anchored sensor generates less artifacts, it can also be uncomfortable or not breathable. Also, the human body changes shape as it moves, providing a challenge for wearable designers to provide an optimum fit to a changeable form.

The present disclosure generally relates to a portable, non-invasive biological and physiological monitoring device coupled with a user's body part and methods for use thereof. While the present technology can be implemented with respect to a user's digit (finger or toe), the present description uses the example of finger for clarity. Instances of describing the object as a ring or other device for coupling with a user's finger can apply to a user's toe. In at least one instance, the device can be a ring. While the present disclosure focuses on implementing the ring with respect to a user's digit (finger or toe), the present disclosure in regards to a ring can also be applied to a user's wrist (for example a bracelet), a user's ankle (for example an anklet), or a user's neck (for example a necklace). Rings have been worn for thousands of years without changes in the basic concept. A typical ring is made with a rigid material which can be difficult to get over knuckles then can be loose once the ring is in place. A stretchable ring typically has poor aesthetics, low breathability, and can cause constriction around the finger circumference if the material is too tight. The ring as described herein can include an adaptive force region that allows a ring worn on a finger to be secure, comfortable, removable, and breathable, without requiring a hinge or change to the outer circumference. In at least one instance, such rings can be used to measure various biometric and physiological data of a user. For example, a ring in accordance with the present disclosure can selectively apply non-Hookean (roughly constant) force to a desired region of the finger, offering a chance to collect biometric data from a compact and comfortable ring.

Biosensing, interactive rings, or jewelry rings worn on fingers or toes, if large enough to fit over the knuckle, may have a loose fit. Additionally, the cross-sectional shape of the finger varies both along its length and with bending motion and with swelling of the finger tissue due to fluid gain or loss. Meanwhile rings with preferred orientation may tend to rotate such that elements of the ring designed to face the back or dorsal side the hand (top) may rotate around to face the inner or palmar (under) side of the finger, and vice-versa. These and other factors can pose a challenge for a ring maker desiring a ring with a stable position. Additionally, the finger cross sectional shape not only varies in diameter and/or moment of inertia, it may vary with movement or position on the finger from round, to oval, to cam-shaped. Furthermore, the palmar side tissue stiffness varies dramatically with finger bend position. The present disclosure provides a biosensing ring with an improved fit. In some examples, the biosensing ring can be used to effectively track biological and/or physiological parameters of a user.

Specifically, FIG. 1 illustrates a ring 100, according to an instance of the present disclosure. As illustrated, the ring 100 can be a ring which is operably engaged with at least a portion of a user's body, such as a finger, a toe, a wrist, an ankle, and/or a neck. The ring 100 can be in the shape of a toroid or an annular cylinder and need not have a circular cross-section or regular shape. As described above, the ring 100 can include one or more sensors 110 disposed on the interior surface of the ring 100. In at least one instance, the one or more sensors 110 are in contact with the skin of the user. For example, some biosensing features are dependent on skin contact. Such sensors 110 can include, but are not limited to, a photoplethysmography (PPG) sensor for detecting heart rate, heart rate variability, other volumetric changes in blood circulation, and spectrum-based blood chemistry measurements such as peripheral oxygenation (SpO2) and perfusion. In some instances, the ring 100 may additionally include sensors 110 to measure other biological and/or physiological parameters including, but not limited to, electrochemical measurements such as biopotential or bioimpedance, bioimpedance spectroscopy, or sweat analysis, skin temperature, and/or the like. For many of these sensors, signal transduction occurs via skin contact. Additionally, certain measurements, such as accelerometer-based measures of tremors or physical activity, the sliding, rotating, and/or rocking of the ring relative to finger can be a source of measurement error. As such, it is exceedingly important to have a ring 100 with consistent, appropriate pressure on the user's finger.

In at least one instance, the ring 100 can be operable to be coupled with an optional output device 150, such as a smartphone (as shown), a smartwatch, computer, mobile phone, handheld device, tablet, personal computing device, a generic electronic processing and displaying unit, cloud storage, and/or a remote data repository via a cellular network and/or wireless Internet connection (e.g. Wi-Fi). The output device 150 can include a display 160 operable to provide a user information and/or data from the one or more sensors 110 regarding various biological and/or physiological parameters. While the sensors 110 are described herein as biological and/or physiological sensors, it should be generally understood that the sensors 110 of the ring 100 disclosed herein can monitor any aspect of a user. The sensors 110 as described herein can include, but are not limited to, an electrodermal (EDA) sensor, a biomechanical sensor, a galvanic skin response (GSR) sensor, a PPG sensor, an electrocardiogram (EKG), an inertial measurement sensor, an accelerometer, a gyroscope, a magnetometer, a global positioning system (GPS), a blood pressure (BP) sensor, a pulse oximetry sensor such as for SpO2, a respiratory rate (RR) monitor, a temperature sensor, a humidity sensor, an audio sensor, an air quality sensor, a microphone, an environmental sensor (including but not limited to ambient noise, light, temperature, air quality, humidity, location, ultraviolet (UV) light exposure level, etc.), and/or any other sensor capable of measuring an aspect of a user and/or their environmental surroundings which may affect the user's physical and/or emotional health or wellbeing.

The output device 150 can include an input control device 165 operable to allow a user to change the display 160 and/or the information and/or data displayed thereon. In at least one instance, the input control device 165 can be a button and/or other actuatable element operable to allow an input to be received by the output device 150. In other instances, the input control device 165 can be a touch sensitive input device including, but not limited to, a touch screen on a smartphone, smart watch, tablet, or the like.

The output device 150 and the ring 100 can be communicatively coupled 130 via a transmitter/receiver 120, 140 disposed on the ring 100 and the output device 150, respectively. The communicative coupling 130 can be a two-way communication pathway allowing the ring 100 to provide information and/or data to the output device 150 and/or the display 160 while similarly allowing the output device 150 to request information and/or data from the ring 100.

The ring 100 can further include a power supply, such as a battery, to supply power to one or more of the sensors 110, transmitter 120, and/or other components in the ring 100.

The fit and/or material of the biosensing ring 100 described above can help ensure that proper measurements are taken. For example in reflective PPG measurements, the mechanical pressure between the sensor and user's skin allows varying blood pressure during a heartbeat cycle to modulate the amount of blood in the skin tissue. Furthermore, the amount of light reflected in the skin from an optical emitter and back from the tissue as read by a photo sensor can depend in part on the pressure of skin contact. Techniques based on ratios of pulsile (AC) and non-pulsile (DC) signal components may be able to cancel some of these effects. However, the pulsile signal itself depends on pressure, so motion artifacts are not fully mitigated even by ratiometric signal analysis. Accordingly, varying levels of pressure against the finger has been a concern for health ring designers. PPG measurements are most effective when taken from soft tissue, and are less effective near bone, so a fixed orientation placing the sensors on the bottom (palmar) side of the finger are more accurate and preferred.

Skin contact is also critical in obtaining accurate skin temperature measurements. For example, skin temperature measurements depend on two thermal conductivities: conductivity to skin and to the environment. Ideally, the conductivity to the skin is much higher than conductivity to the environment, so the measured temperature is mostly dependent on the skin temperature, not the air temperature. This conductivity is heavily dependent on the relationship of the contact between the user's finger and the biosensing ring.

Furthermore, electrical measurements are perhaps the most sensitive to changes in skin contact area and pressure. Conductivity through skin can depend on the area of the electrode of the sensor in contact with the skin. Additionally, conductivity through the skin can depend on the pressure the sensor is exerting on the user. The stability of the contact and the compression of the various skin layers, including the strateum corneum and epidermis and sweat glands, can be dependent on the area and pressure of contact. The region of the finger contacted by the biosensing ring can also significantly effect measurements. For example, sweat glands for sensing emotional arousal such as stress events are primarily on the palmar side. As such, the orientation of the biosensing ring with respect to a user's hand is also important in obtaining accurate measurements.

In at least one instance, a biosensing ring 100 such as that described herein can include user-interactive features such as a display, LED indicators, touch control, and the like. Such features may be designed to face the dorsal (back) side and/or portion of the hand. Such features tend to have less contact with objects being manipulated by the hand and may be more visible to a user. Alternatively, a biosensing ring 100 can be designed having certain features on the palmar (underside) of the finger to be hidden from view while the ring 100 is being worn. In at least some instances, the ring 100 can include ornamental features such as a gem or design, which is intended to be visible. In all cases, the orientation of the ring 100 can be crucial to the product aesthetics or use as a biosensor 10.

As discussed above, a major problem with rings, in general, is that the knuckles or joints of the fingers are often larger in diameter than the areas between the joints, for example bone segments. In order to be worn, a ring must fit over the knuckle. A conventional rigid ring can be loose when resting between the joints of the finger. While rings made of stretchable material are known in the art, such materials can often be problematic when combined with electronics. For example, flex circuit traces, rigid-flex joints, circuit component solder joints, or wire to flex joints on printed circuit boards are prone to failure when subjected to repeated deformation. From this perspective a rigid ring 100 is desirable. Moreover, a ring that is capable of being stretched can result in inequivalent pressure placed at various points on the user's finger. For example, as the ring stretches, the pressure it exerts can increase in accordance with Hooke's law. This practically limits the range of stretching as the force can become uncomfortable after a certain level of stretching has been reached. Furthermore, a stretched elastic material can provide higher contact force than an un-stretched material, which is nonideal.

The ring 100 as described herein provides a "fit" on a finger similar to that of a rigid ring but also provides the appropriate pressure and flexibility for biosensing devices. In at least one instance, such ring 100 must allow for a fit that is narrower than the ring's cross section and a finger which itself changes (e.g. when a finger is bent or stretched). Additionally, such ring 100 can also present a more similar force to the finger during motion and which preserves the desired ring orientation. A biosensing ring 100 as described herein provides a ring 100 having one or more adaptive force regions capable of providing such benefits.

Figure 2A:
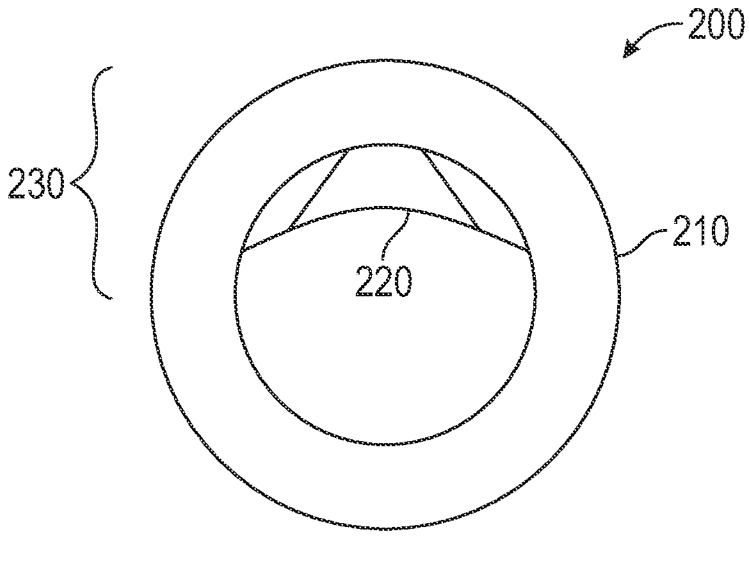
FIG. 2A is a diagrammatic view of a ring, according to at least one instance of the present disclosure.
Figure 2B:
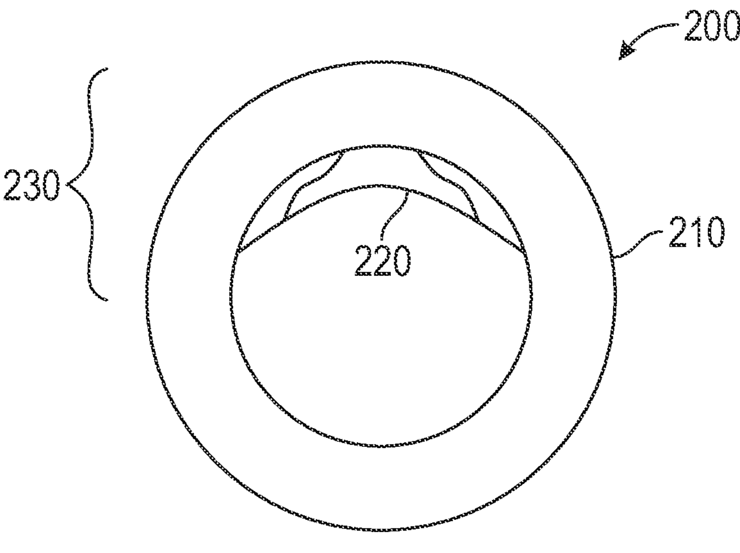
FIG. 2B is a diagrammatic view of a ring, according to at least one instance of the present disclosure.

FIGS. 2A and 2B illustrate cross-sectional views of a biosensing ring 200, 250 as described herein. For example, FIG. 2A illustrates the biosensing ring 200 having a wall 210 with an adaptive force region 230. The adaptive force region 230 can be operable to exhibit non-Hookean deformation. The adaptive force region 230 can include an adjustable structure 220 which is configured to work as a ring sizing element. The biosensing ring 200 as illustrated in FIG. 2A shows the adaptive force region 230 in a relaxed position. The adaptive force region 230 can be located on an inner portion of the toroid and a Hookean region can be located on the inner portion of the toroid. The adaptive force region 230 can be only a portion of the toroid with the remainder of the toroid being a Hookean region. In at least one example, the Hookean region is opposite the adaptive force region 230. FIG. 2B illustrates the same biosensing ring 200 wherein the adaptive force region 230 is in a deformed state. The adjustable structure 220 can deform such that a joint or knuckle can pass through the ring, or in some instances the adjustable structure 220 can deform as the finger the biosensing ring 200 is on bends or moves. As shown, the wall 210 of the biosensing ring does not change, thus maintaining consistent pressure around the finger, while the adjustable structure 220 bends to allow for comfortable movement. FIGS. 2A and 2B illustrate one instance of intersecting sheets which buckle when subjected to a force. For example, as the inner support begins to buckle it reduces the spring constant by allowing wider deformation.

Figures 3A, 3B, 3C:
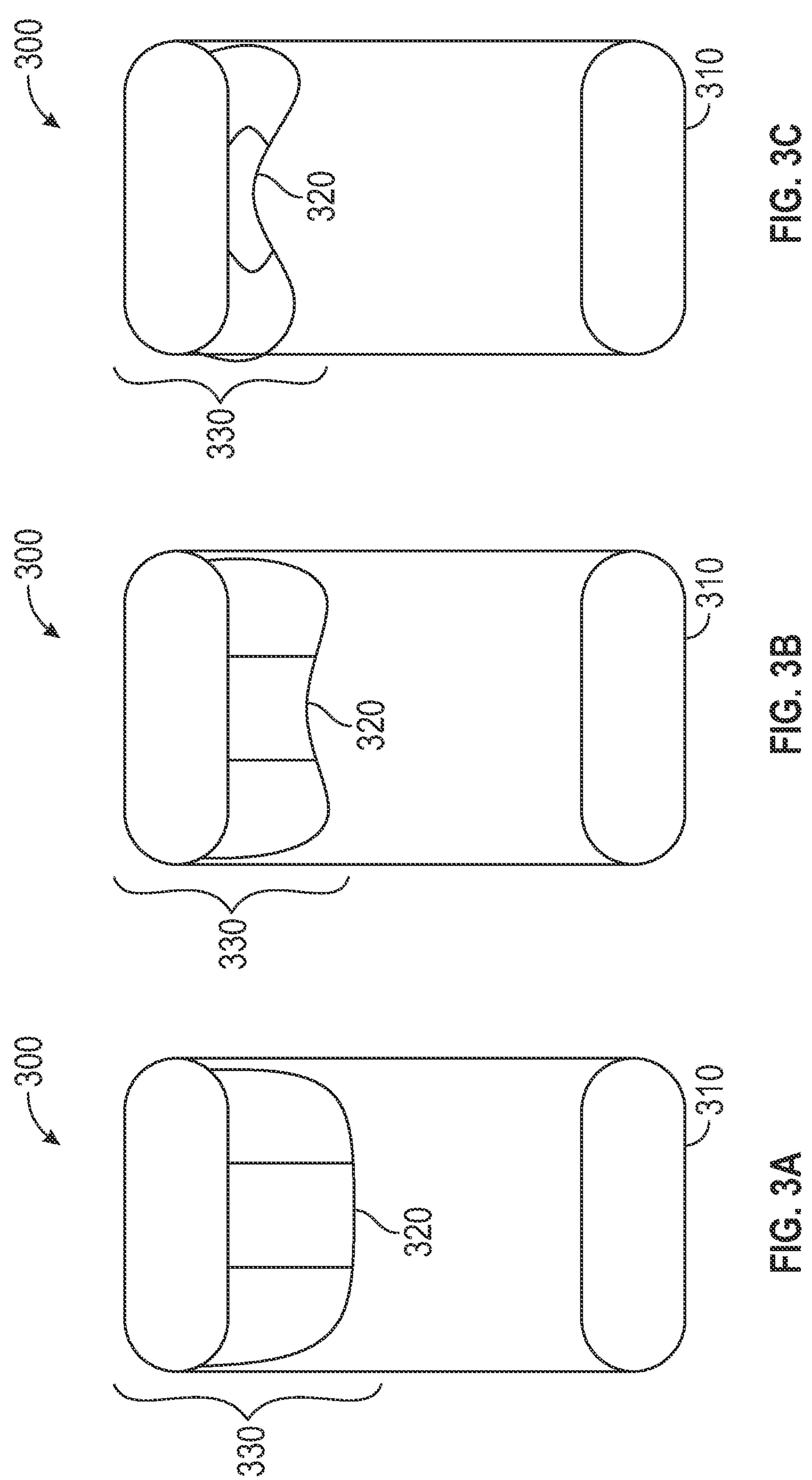
FIG. 3A is a diagrammatic representation of a cross-sectional view of a ring in various states of deformation, according to at least one instance of the present disclosure.
FIG. 3B is a diagrammatic representation of a cross-sectional view of a ring in various states of deformation, according to at least one instance of the present disclosure.
FIG. 3C is a diagrammatic representation of a cross-sectional view of a ring in various states of deformation, according to at least one instance of the present disclosure.

FIGS. 3A-3C illustrate cross-sectional views of a ring 300 in accordance with the present disclosure taken across a different axis than FIGS. 2A and 2B. As described above, the ring 300 can include a wall 310 and an adaptive force region 330 having an adjustable structure 320. FIGS. 3A-3C illustrate the deformation of the adjustable structure 320 of the adaptive force region 330 as force is exerted on the region. As the adjustable structure 320 begins to bend and buckle, the deformation extends to the outer edges of the adjustable structure 320, reducing the spring constant. In at least one instance, the adjustable structure 320 can include a pattern of extruded polygons (for example, rectangular cells, honey combs, etc.), cilica or finger-like protrusions extending in a radial direction, extensions in the radial direction (including, but not limited to, extending along the finger (proximal to distance) and extending around the finger (circumferentially)), buckling sheets of a compliant material (in at least one instance, the sheets containing a thin cross section as compared to their length allowing the bending moment to be lowest in one of the axial direction or the cross-section through a circumferential cross-section), and the like. The extensions in the radial direction can be fence-like. In at least one instance, the adaptive force region 330 can further include a cam-like torsion member, which allows the ring to twist to fit over larger sections of the finger such as a joint or knuckle, then twists back to the original position.

The adaptive force region 230 of the ring 200 allows for non-Hookean deformation of the material. An example of non-Hookean deformation of a material includes buckling, sliding, or rotating. For example, a cam in a compound bow allows the force required to stretch the bow to not increase linearly near the end of the draw so as to relieve some strain on the archer in the aiming position. For a given force, a cantilever that is pinned at two ends bends far less than one pinned at only one end. Therefore, a device which allows sliding at the point of compression when a friction coefficient is exceeded provides a non-Hookean behavior. In at least one instance, a structure made of extruded intersecting planes of compliant material (like a rectangular honeycomb of a rubber material) can exhibit buckling. This is used in some cushions and mattresses such that the point of greatest deformation isn't necessarily the point of greatest force. A memory foam or a piston with a controlled release valve is another non-Hookean material. They provide resistance to deformation which decays with time.

Figures 3D, 3E, 3F, 3G, 3H, 3I, 3J, 3K:
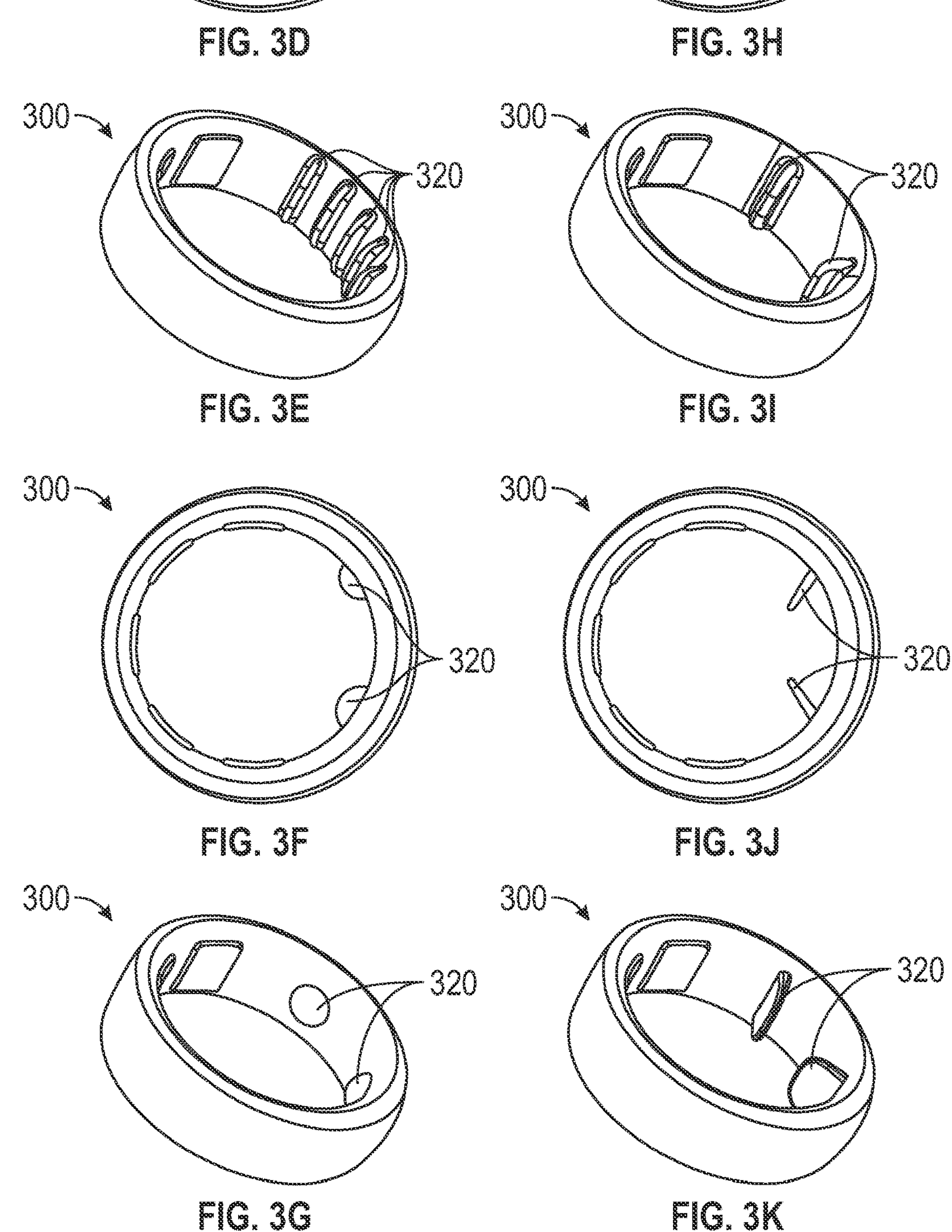
FIGS. 3D and 3E are diagrammatic views of a ring having five adjustable structures extending in a radial direction, according to at least one instance of the present disclosure.
FIGS. 3F and 3G are diagrammatic views of a ring having two adjustable structures extending in a radial direction, according to at least one instance of the present disclosure.
FIGS. 3H and 3I are diagrammatic views of a ring having two adjustable structures extending in a radial direction, according to at least one instance of the present disclosure.
FIGS. 3J and 3K are diagrammatic views of a ring having two adjustable structures extending in a non-radial direction, according to at least one instance of the present disclosure.

FIGS. 3D and 3E are diagrammatic views of a ring 300 having five adjustable structures 320 extending in a radial direction, according to at least one instance of the present disclosure. FIG. 3D is a view in the axial direction of ring 300 and FIG. 3E is an isometric view of the ring 300 of FIG. 3D. As illustrated the five adjustable structures 320 extend in a radial direction. The Five adjustable structures 320 are configured to have a curvilinear surface on the inner surface (portion for contacting a user). The inner surface is configured that middle portion has a greater height than the outer portion. As illustrated the adjustable structures 320 have a height in the radial direction that is smaller than other examples provided herein. In one configuration, the number of the adjustable structures 320 can be increased and the height decreased.

FIGS. 3F and 3G are diagrammatic views of a ring 300 having two adjustable structures 320 extending in a radial direction, according to at least one instance of the present disclosure. FIG. 3F is a view in the axial direction of ring 300 and FIG. 3G is an isometric view of the ring 300 of FIG. 3F. The two adjustable structures 320 are configured as a dome structure. The dome structure allows for a greater force to be exerted near the bisecting plane of the ring 300, but allowing deflection near the edges of the ring 300. The height of the dome can be greater than the height of the curvilinear structures of FIGS. 3D and 3E.

FIGS. 3H and 3I are diagrammatic views of a ring 300 having two adjustable structures 320 extending in a radial direction, according to at least one instance of the present disclosure. FIG. 3H is a view in the axial direction of ring 300 and FIG. 3I is an isometric view of the ring 300 of FIG. 3H. The two adjustable structures 320 as illustrated are similar in shape to the structures of FIGS. 3D and 3E except that the height of the adjustable structures are greater than that of FIGS. 3D and 3E and there are two of the adjustable structures 320 rather than five. The adjustable structures 320 are located at the same position as the two outermost adjustable structures of FIGS. 3D and 3E.

FIGS. 3J and 3K are diagrammatic views of a ring 300 having two adjustable structures 320 extending in a non-radial direction, according to at least one instance of the present disclosure. FIG. 3J is a view in the axial direction of ring 300 and FIG. 3K is an isometric view of the ring 300 of FIG. 3J. The adjustable structures 320 of FIGS. 3J and 3K differ from the others illustrated in that the structures extend in a non-radial direction. The extension in the non-radial direction has an advantage in the fit of a user, but it might result in more difficulty in actual molding of the adjustable structures 320.

Figure 3L:
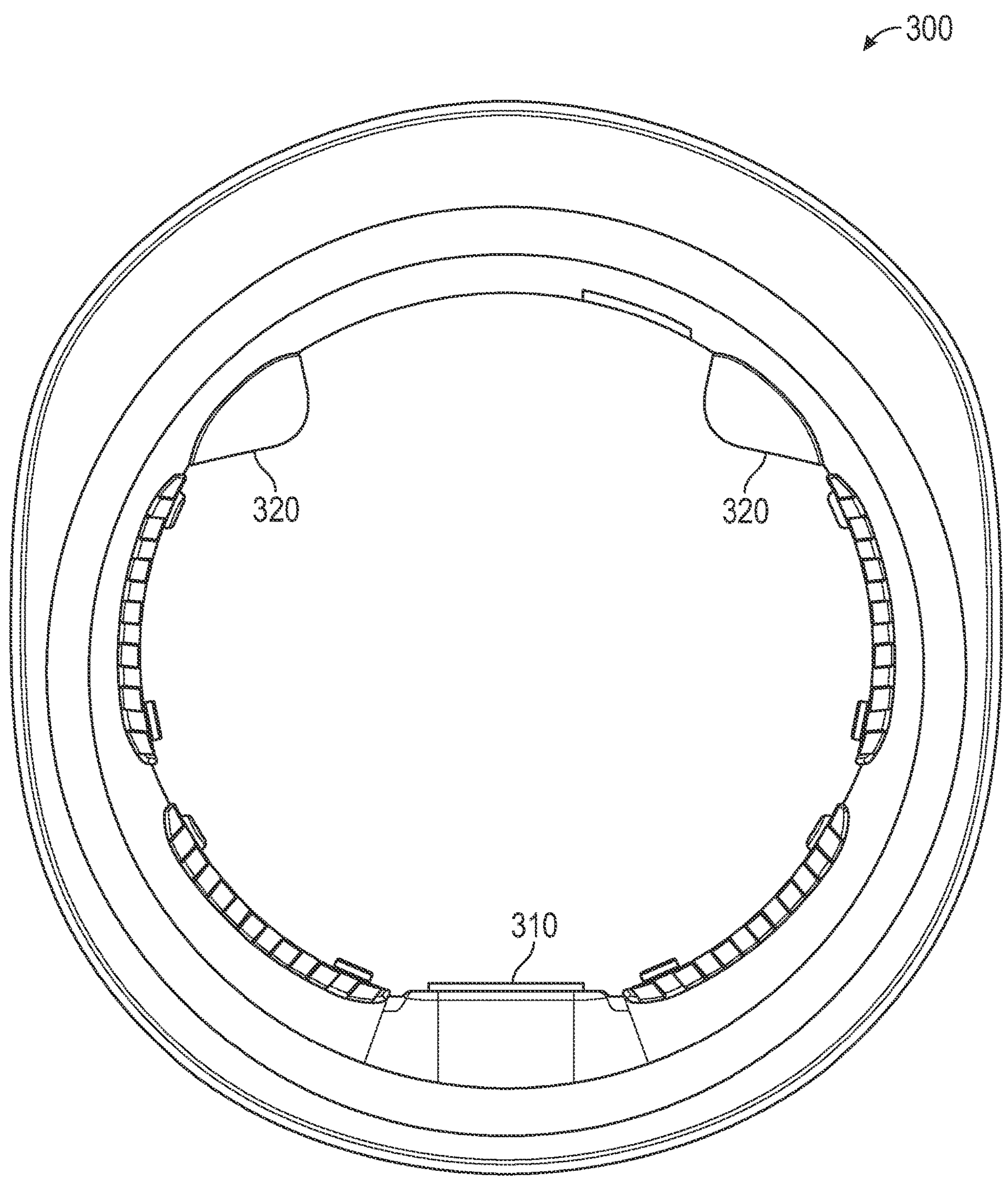
FIGS. 3L, 3M, 3N, 3O, and 3P are diagrammatic views of a ring having two adjustable structures extending towards a center of the ring, according to at least one instance of the present disclosure.
Figure 3M:
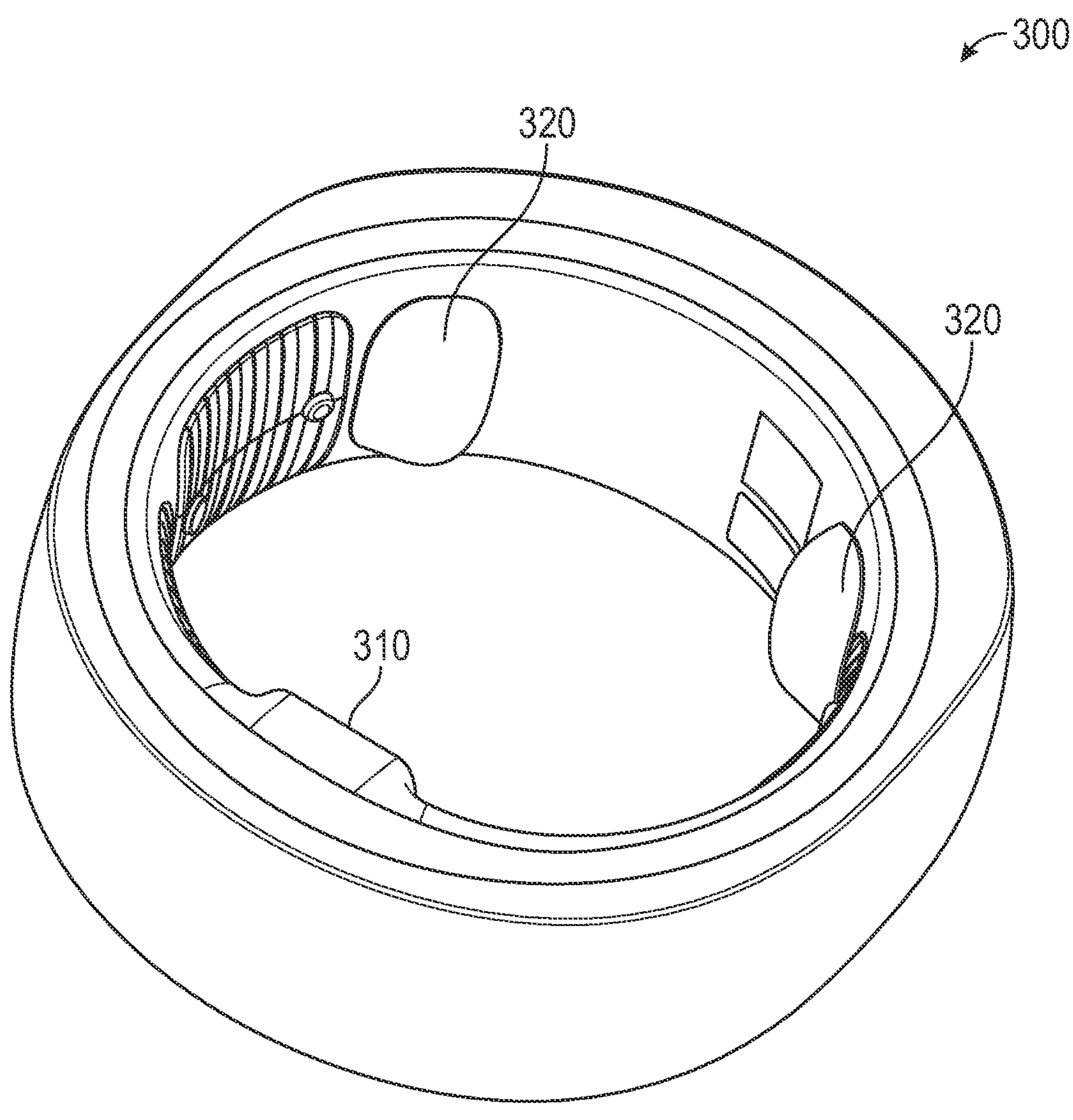
Figure 3N:
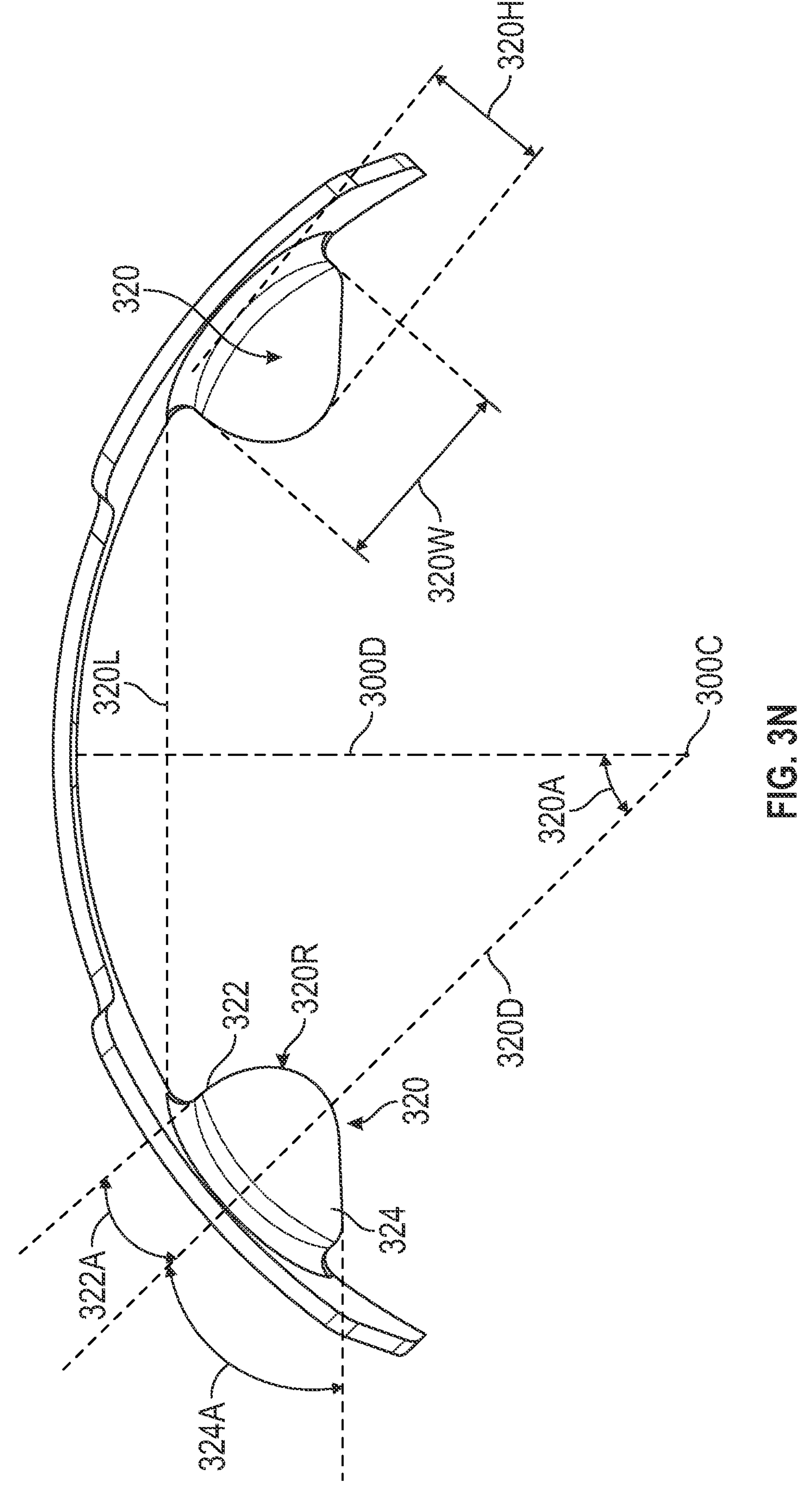
Figure 3O:
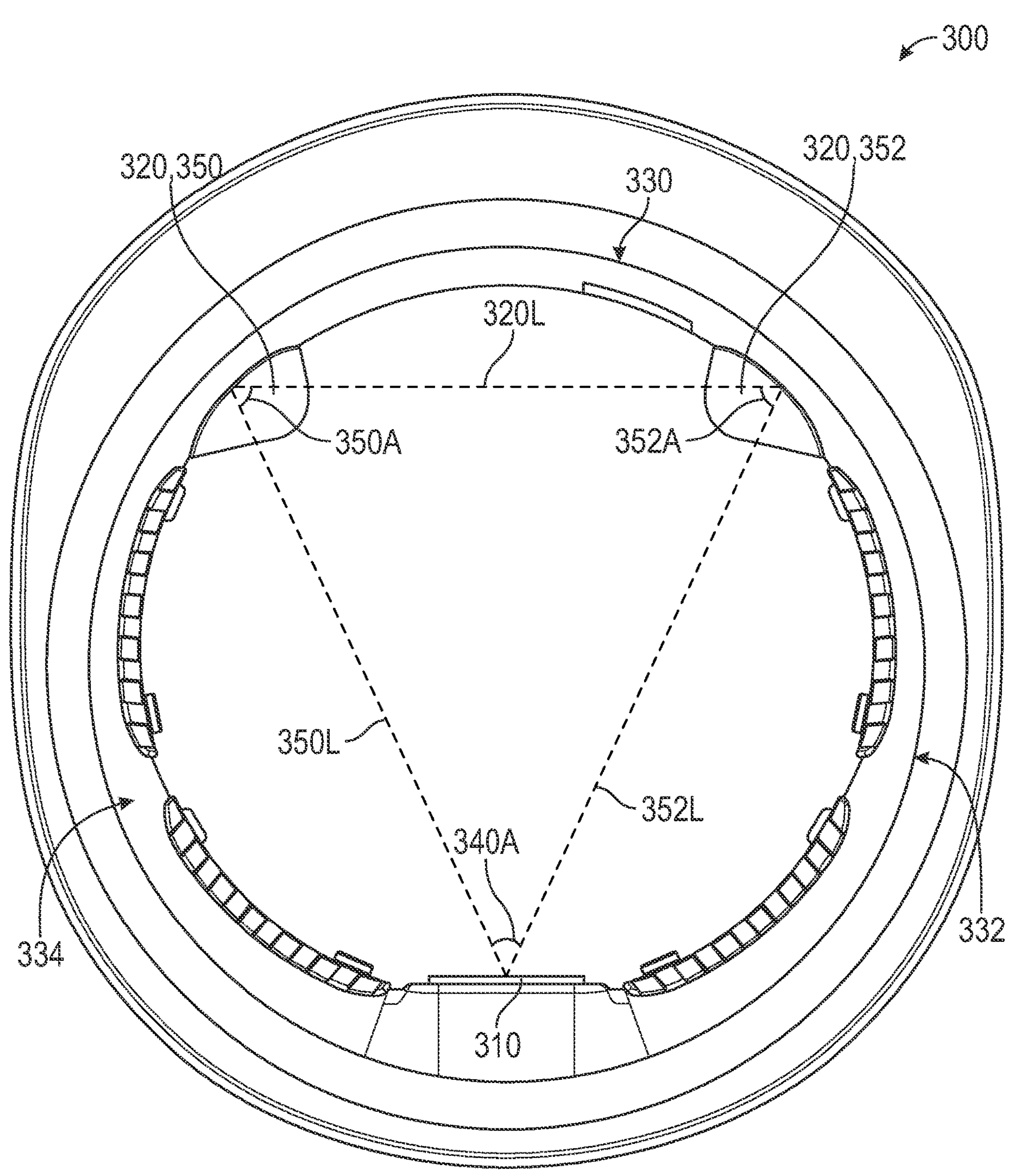
Figure 3P:
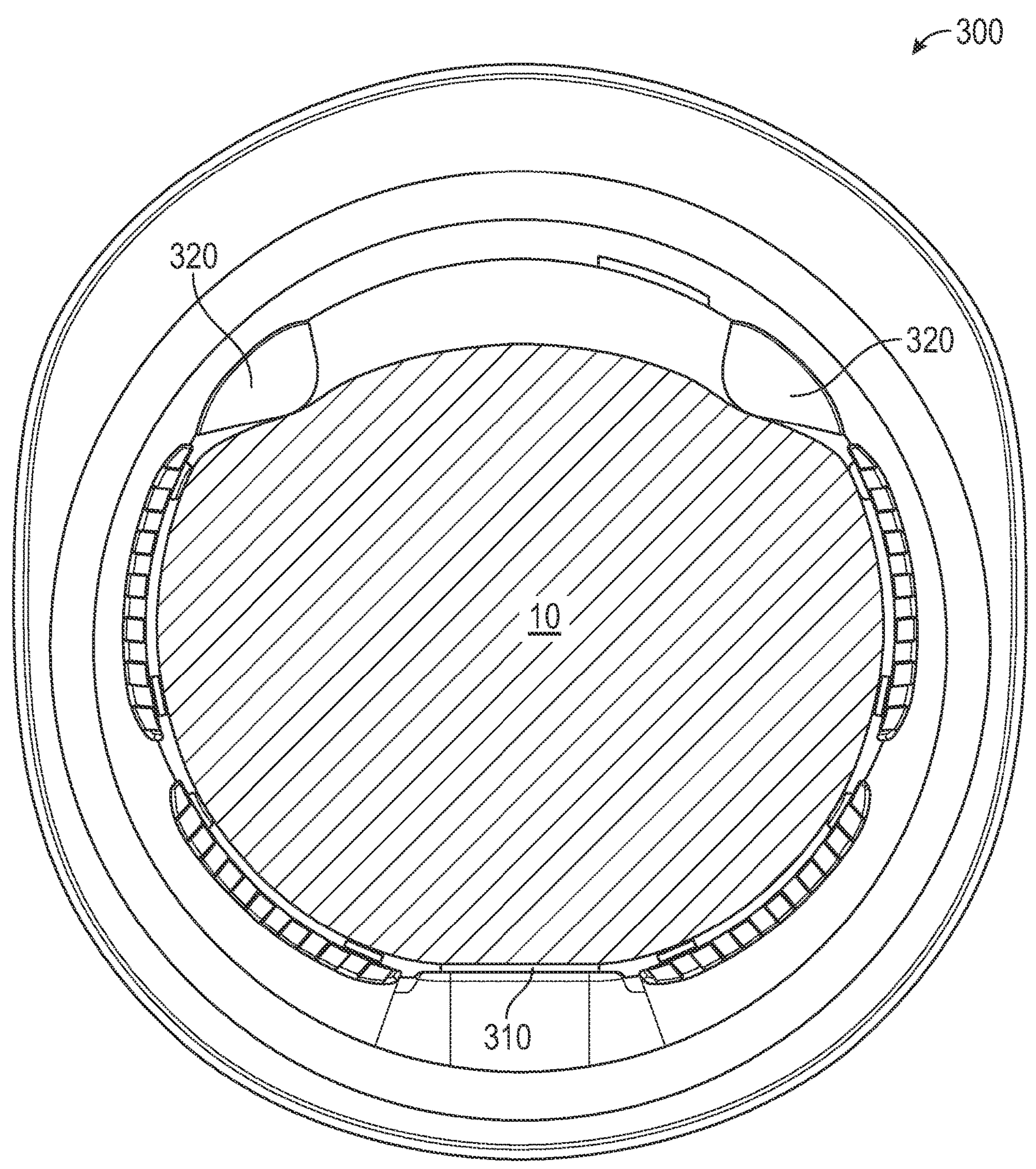

FIGS. 3L-3P are diagrammatic views of a ring 300 having two adjustable structures 320 extending from the inner portion of the ring 300, according to at least one instance of the present disclosure. FIG. 3L is a view in the axial direction of ring 300. FIG. 3M is an isometric view of the ring 300 of FIG. 3L. FIG. 3M is an enlarged view of the portion of the ring 300 including the adjustable structures 320. FIG. 3O is another view in the axial direction of ring 300. FIG. 3P is a cross-sectional view of the ring 300 of FIG. 3L with a finger disposed therein.

The adjustable structures 320 of FIGS. 3L-3P substantially extend from the inner portion of the ring 300. In some examples, the adjustable structures 320 extend substantially in a direction towards the sensor(s) 310 of the ring 300. Accordingly, the adjustable structures 320 are operable to maintain the position of the finger 10 in relation to the sensor(s) 310. As illustrated in FIGS. 3L-3P, there are two adjustable structures 320 extending from the inner portion of the toroid ring 300. While the shape of the adjustable structures 320 illustrated in FIGS. 3L-3P are an irregular shape, in some examples, the shape of the adjustable structures 320 can be other shapes not shown. As shown in FIGS. 3L-3P, the adjustable structures 320 are positioned in the ring 300 opposite the sensor(s) 310 in relation to the center 300C of the ring 300. Accordingly, as shown in FIG. 3P, the adjustable structures 320 are positioned to abut against the finger 10 to push the finger 10 and/or maintain the position of the finger 10 against the sensor(s) 310 of the ring. For example, the sensor(s) 310 may be operable to be positioned against the underside (palm side) of the finger 10. The adjustable structures 320 can be size, shaped, and/or positioned to resist and/or prevent rotation and maintain position and contact of the finger 10 in relation to the sensor(s) 310.

As illustrated in FIG. 3N, the adjustable structures 320 can have an irregular shape to better interact with the finger 10 to maintain position and prevent rotation of the finger 10 while the ring 300 is disposed on the finger 10 or other body part. As illustrated in FIGS. 3L-3P, the adjustable structures 320 can each be substantially identical in size and/or shape. As illustrated in FIGS. 3L-3P, the adjustable structures 320 can mirror one another about a central ring axis 300D which extends from the body of the ring 300 through the center 300C of the ring 300 and the sensor(s) 310. A structure direction 320D can extend through the adjustable structures 320 and the center 300C of the ring 300. In some examples, an angle 320A formed by the structure direction 320D and the central ring axis 300D can be between about 25 degrees and about 85 degrees. In some examples, the angle 320A can be between about 30 degrees and about 70 degrees. In some examples, the angle 320A can be between about 40 degrees and about 50 degrees. In some examples, the angle 320A can be about 45 degrees. With a larger angle 320A, the larger the distance 320L is between the adjustable structures 320. The desired angle 320A and distance 320L between the adjustable structures 320 allows for more efficient and more comfortable maintenance of the finger 10 in the desired position while providing the desired force against the finger 10 to press the finger 10 towards the sensor(s) 310.

As illustrated in FIG. 3N, the adjustable structures 320 can include a first side 322 and a second side 324. In at least one example, the first side can face in a direction away from the sensor(s) 310 and the second side 324 can face the sensor(s) 310. The first side 322 can be arranged relative to the second side 324 such that the first side 322 is located further from the sensor(s) 310 in a circumferential direction. The circumferential direction can begin from the sensor(s) 310. The circumferential direction is directed towards the adjustable structure 320 in that the shortest circumferential distance between the sensor(s) and the adjustable structure 320 is considered. For example, the circumferential direction may begin at the sensor(s) 310 and move toward the adjustable structure 320 in the same hemisphere as the sensor(s) 310 along the inner circumference of the toroid ring 300. Therefore, the first side 322 can be described as being distal from the sensor(s) 310 in a circumferential direction of the ring 300, and the second side 324 can be described as being proximal to the sensor(s) 310 in a circumferential direction of the ring 300. The first side 322 can have a slope that extends in relation to the structure direction 320D at a first angle 322A. The first angle 322A can be between about 1 degree and about 25 degrees. In some examples, the first angle 322A can be between about 5 degrees and about 15 degrees. In some examples, the first angle 322A can be about 10 degrees. The second side 324 can have a slope that extends in relation to the structure direction 320D at a second angle 324A. The second angle 324A can be between about 20 degree and about 75 degrees. In some examples, the second angle 324A can be between about 35 degrees and about 60 degrees. In some examples, the second angle 324A can be about 50 degrees.

In some examples, as illustrated in FIGS. 3L-3P, the first angle 322A is smaller than the second angle 324A. Accordingly, each of the adjustable structures 320, mirroring one another about the central ring axis 300D, can prevent outward rotation of the finger 10 in the respective directions of each of the adjustable structures 320. In other words, the adjustable structures 320 can prevent rotation of the finger 10 in the direction towards the second side 324 of each the adjustable structure 320. In some examples, the first angle 322A In some examples, the first angle 322A can be larger than the second angle 324, so that the adjustable structures 320 prevent rotation of the finger 10 in the direction towards the first side 322 of each of the adjustable structures 320.

The adjustable structures 320 can extend along the structure direction 320D towards the center 300C of the ring 300 to have a height 320H. In some examples, the height 320H can be between about 1 millimeter and about 4 millimeters. In some examples, the height 320H can be between about 1.5 millimeters and about 2.5 millimeters. In some examples, the height 320H can be about 1.95 millimeters.

In some examples, the adjustable structures 320 can have a width 320 W between about 1.5 millimeters and about 5 millimeters. In some examples, the adjustable structures 320 can have a width 320 W between about 2.5 millimeters and about 4 millimeters. In some examples, the width 320 W can be about 3.1 millimeters.

In at least one examples, the first side 322 and the second side 324 can be connected by a curvature with a radius of curvature 320R. The radius of curvature 320R can be such that the adjustable structures 320 are comfortable against the finger 10. Accordingly, the adjustable structures 320 do not dig into the finger 10 and allow the finger 10 some movement and/or rotation until the desired position of the finger 10 is achieved.

The shape and positioning of the adjustable structures 320 in relation to the sensor(s) 310 is critical to provide a comfortable force against the finger 10 towards the sensor(s) 310 as well as prevent rotation of the finger 10. In at least one example, the ring 300 can be circumferentially split into three sections 330, 332, 334 by the adjustable structures 320 and the sensor(s) 310. Section 330 can be formed between the two adjustable structures 320. Section 332 can be formed between adjustable structure 352 and the sensor(s) 310. Section 334 can be formed between adjustable structure 350 and the sensor(s) 310. In at least one example, sections 332, 334 can be substantially the same size. In some examples, the sections 332, 334 can be different sizes. The sizes of the sections 330, 332, 334 can be adjusted to provide a comfortable fit while preventing rotation of the finger 10 and maintaining the position of the finger 10 in relation to the sensor(s) 10.

In at least one example, as illustrated in FIG. 3O, the adjustable structures 320 and the sensor(s) 310 can form a triangle. In at least one example, the distance 350L between adjustable structure 350 and the sensor(s) 310 can be substantially the same as the distance 352L between adjustable structure 352 and the sensor(s) 310. In some examples, the distance 350L and the distance 352L can be different. In at least one example, the angle 350A formed by distance 320L between the two adjustable structures 350, 352 and the distance 350L can be substantially the same as the angle 352A formed by distance 320L and the distance 352L. In some examples, the angle 350A can be different than the angle 352A. The larger the distance 320L is corresponds with a larger angle 340A formed by distance 350L and distance 352L. Conversely, the smaller the distance 320L is corresponds with a smaller angle 340A.

Figure 4:
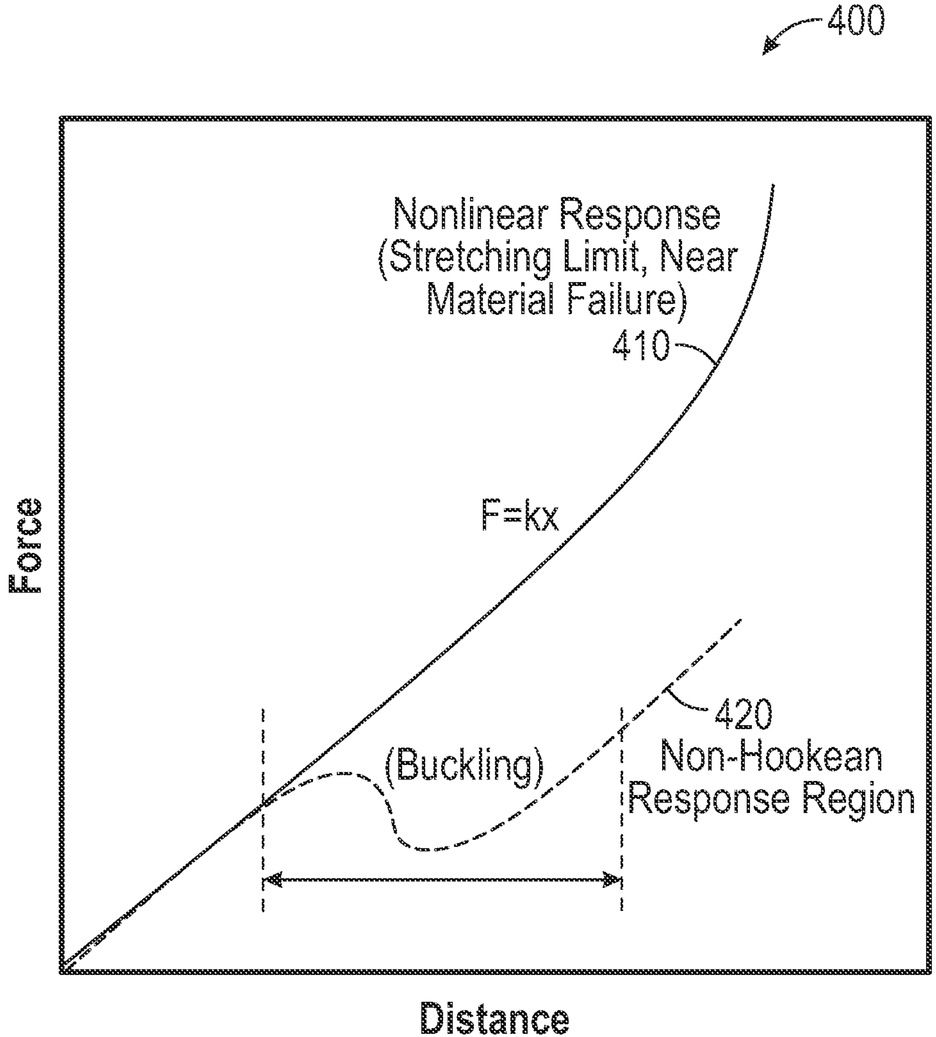
FIG. 4 is a diagrammatic representation of Hookean and non-Hookean material response to a force, according to at least one instance of the present disclosure.

FIG. 4 illustrates a diagrammatic representation 400 of materials illustrating Hookean 410 and non-Hookean 420 response to pressure (force) of a distance. The adjustable structure as described with respect to FIGS. 2A-2B and 3A-C can be made in this manner.

In at least one instance, the adaptive force region can lie between a rigid portion of the ring and the dorsal side and/or portion of the finger. Such arrangement can allow for sensing instrumentation on the portion of the biosensing ring facing the underside (palm side) of the finger. The adaptive force region can buckle under pressure, allowing the biosensing ring to be moved over the joint or knuckle and still provide a desirable level of force to hold the ring in place on the midsection of the proximal phalanx (the place where rings usually sit). Possible utilities of such a feature can include, but are not limited to, reduced rolling of a weighted dorsal side and/or portion of the ring (such as where electronics or ornamental features add weight to a portion of the ring) due to the friction provided by the ring-skin contact, reduce slipping of the ring along the proximal-distal direction, increased ease of ring removal and replacement (such as removal for recharging or rings which are not worn at all times), reduced rocking of the ring about an axis transverse to the long direction of the phalanx, consistent pressure between the palmar side of the finger and the inner side of the ring (including maintaining appropriate pressure for biosensing applications), reduced motion artifacts with respect to accelerometer/gyroscope-based motion and activity sensing, and the like. The dorsal side and/or portion of the ring refers to a side and/or portion of the ring that is positioned on the dorsal side of the finger or hand.

In at least one instance, a biosensing ring in accordance with the present disclosure will deform more easily than it stretches. In a sense, a silicone ring can be considered adaptive. However, because of the features described herein, the biosensing ring will first shape to finger and then stretch. This means that a fitted ring is in contact with the entire circumference of the finger. The adaptive force region 230 as described does not allow for increased pressure to occur on some parts of a finger and reduced pressure on others. When the entire circumference of a digit or extremity is compressed it can reduce comfort and limit blood flow. Accordingly, the biosensing ring includes an adaptive force region 230 and a rigid region, such as a wall 210, to maintain appropriate pressures. In an example, the adaptive force region 230 can face the dorsal side of the finger, and the restoring force pushes the ring in the dorsal direction, not radially around the entire circumference. Such movement allows the adaptive force region to change without adjusting the sides of the ring, constricting the finger completely, and/or to allowing the finger soft tissues to flex outwards as the palmar-facing side of the ring is held in contact with underside of the finger. Not only can such design provide a more comfortable ring, it can allow for better airflow. The dorsal side of the finger has less blood flow (e.g. mostly skin and bone) so pressure there is less of a concern for comfort, similar to the way watch faces typically rest on the bones of the wrist, rather than the anterior side where shape changes occur with hand motion.

Figure 5:
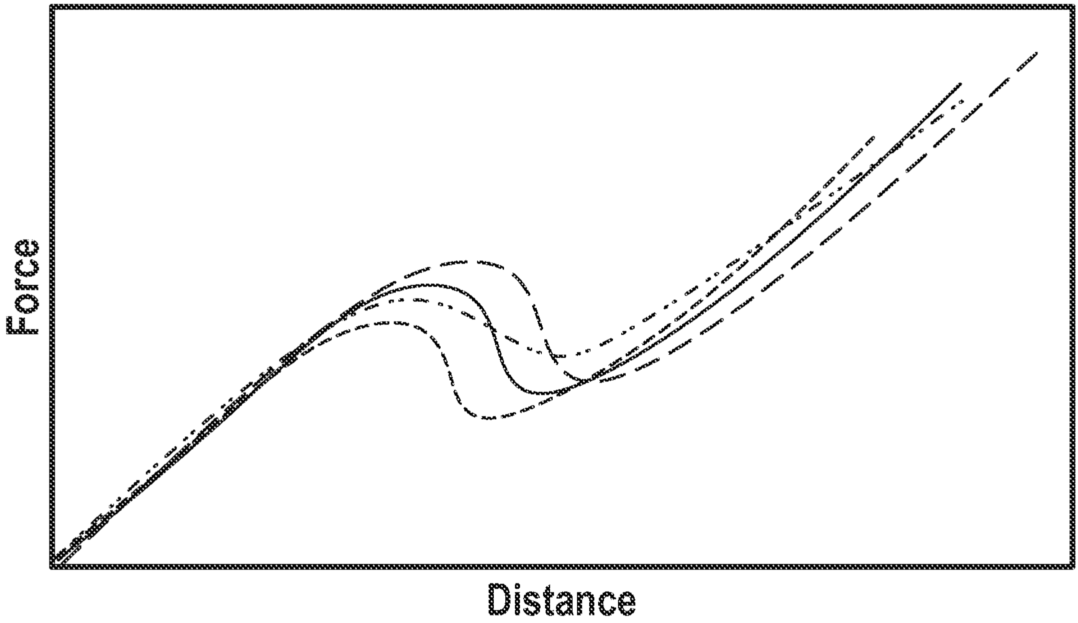
FIG. 5 is a diagrammatic representation of an ensemble of non-Hookean members response to a force, according to at least one instance of the present disclosure.

In an example, the biosensing ring 200 can be a rigid or quasi-rigid ring with an adaptive force component, such as adjustable structure 220, in an adaptive force region 230 as illustrated in FIGS. 2A and 2B. As indicated above, the biosensing ring 200 can be in the shape of a toroid and the toroid can be made of a rigid material or a quasi-rigid material. In at least one instance, the hardness of the quasi-rigid material can be measured in Durometers. A Durometer is an international standard for measuring the hardness of rubber, plastic, and most non-metallic materials. Hardness, respectively, is a material's resistance to a surface indentation. A quasi-rigid material as described herein can be any material that is between extra soft and extra hard. The biosensing ring 200 can be rigid in the sense that changing the outer circumference of the ring requires significantly more force than is required to reach the non-Hookean response of the adaptive force component 230. In at least one instance, the adaptive force component 230 is an ensemble of compliant members with varied thresholds for non-Hookean behavior. This allows for a quasi-constant force region. In at least one instance, quasi-constant force may refer to an area of the material which can exhibit different force profiles at different times or positions. FIG. 5 illustrates a diagrammatic representation of an ensemble of non-Hookean members. As shown, the ensemble response function (dot-dot-dash) curve is flatter than the curves indicating individual non-Hookean complaint members.

Figure 6A:
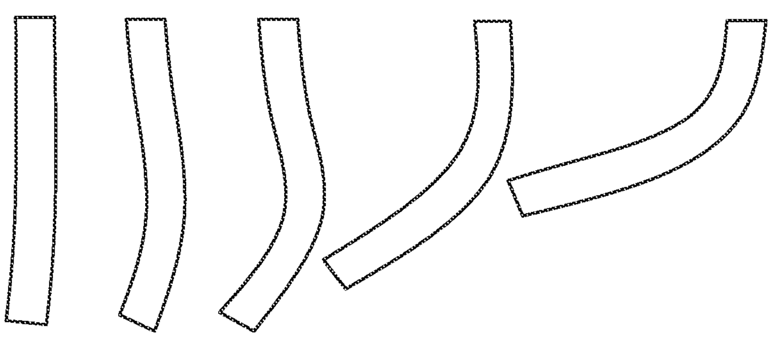
FIG. 6A is a diagrammatic representation illustrating deflection in a non-Hookean component, according to at least one instance of the present disclosure.

FIG. 6A illustrates cross-sectional views of an exemplary a non-Hookean component. As shown, the component, such as a wall of a biosensing ring, may attempt to compress, then bend, then slide and bend when it experiences friction. The transition from compression to dual-clamped to single-clamped cantilever provides a non-Hookean response. The threshold for buckling usually involves a shear or torsion instability, so shear force in the form of a user attempting to pull a ring onto their finger allows for natural buckling as the rings comes into place on the finger.

Figure 6B:
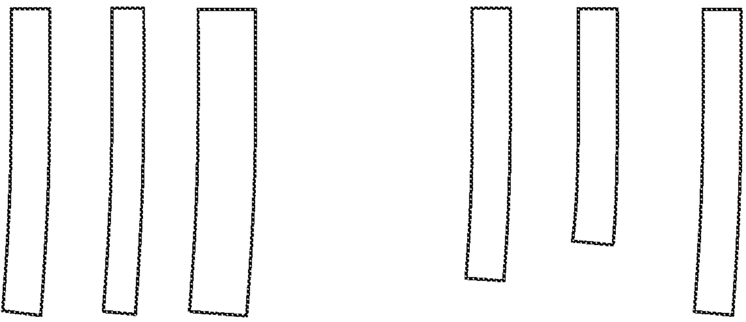
FIG. 6B is a diagrammatic representation illustrating deflection in an ensemble of non-Hookean components, according to at least one instance of the present disclosure.

In at least one instance, an ensemble of non-Hookean components can be made by varying the component's critical dimensions, including length, cross-sectional area, thickness, and/or material composition. FIG. 6B illustrates cross-sectional views of an exemplary ensemble of non-Hookean components. The slope of the force-distance curve affects how much a biometric measurement is affected by changes in the finger shape or increases in force, (e.g. acceleration from motion). The constant force level is set by the design of the adaptive force region and the size of the ring relative to the finger and can be designed for a compromise of comfort and stability. Specifically, the adaptive force region of the biosensing ring can act like an active ring re-sizer. As such, the adaptive force region can continuously adjust in deformation as the user wears the ring, without requiring elements which slide into each other, as this is not good for electronics and tends to pinch the finger, which has high tactile sensitivity.

Figure 7:
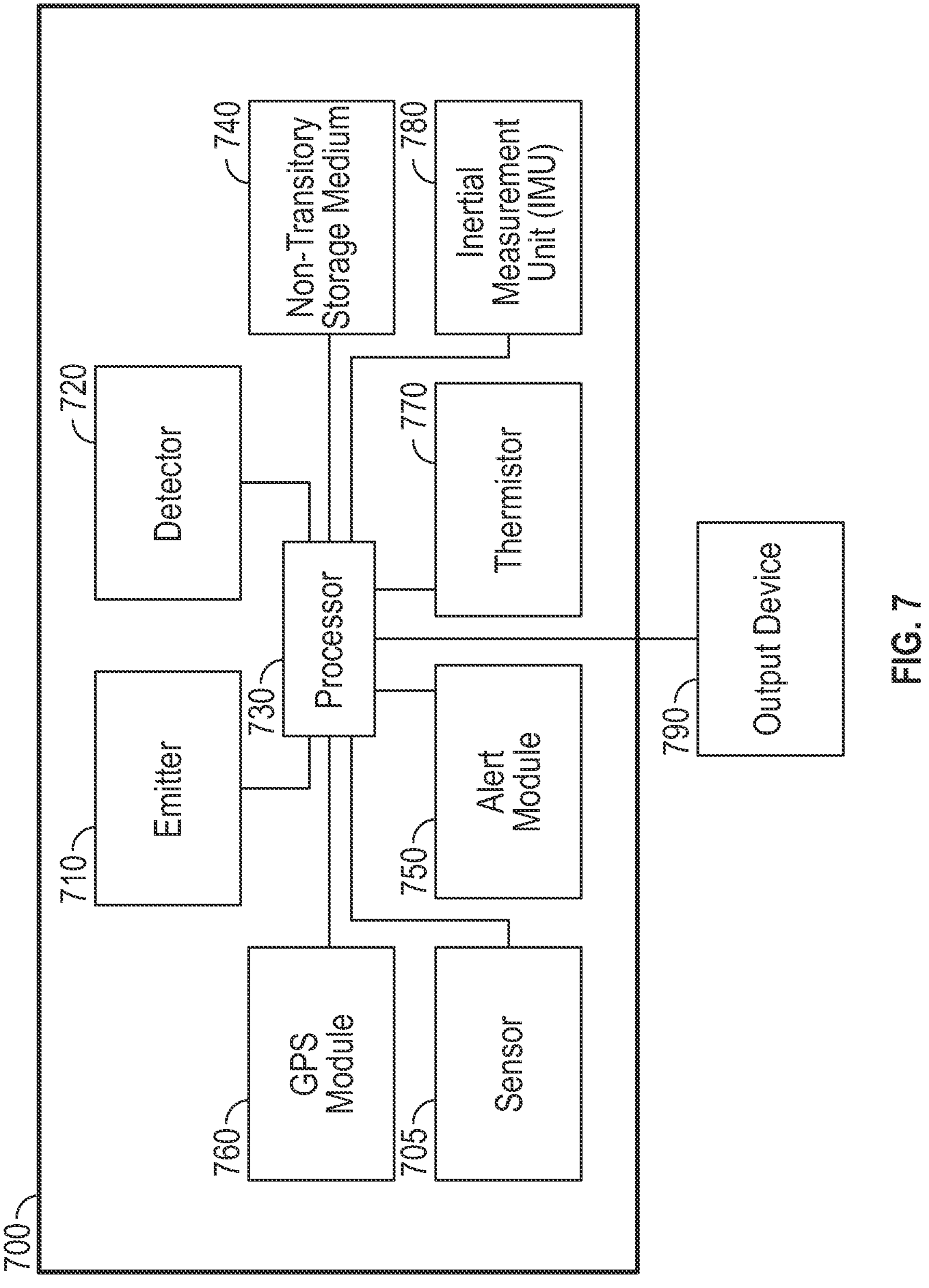
FIG. 7 is a block diagram of a ring, according to at least one instance of the present disclosure.

FIG. 7 illustrates the components of a ring 700 according to at least one instance of the present disclosure. As shown in FIG. 7, the ring 700 can include an emitter 710 and detector 720, which can be communicatively coupled to a processor 730. The processor 730 can be communicatively coupled to a non-transitory storage medium 740. The ring 700 can be coupled to an output device 790.

The emitter 710 delivers light to the tissue and the detector 720 collects the optically attenuated signal that is back-scattered from the tissue. In at least one instance, the emitter 710 can be configured to emit at least three separate wavelengths of light. In another instance, the emitter 710 can be configured to emit at least three separate bands and/or ranges of wavelengths. In at least one instance, the emitter 710 can include one or more light emitting diodes (LEDs). The emitter 710 can also include a light filter. The emitter 710 can include a low-powered laser, LED, or a quasi-monochromatic light source, or any combination thereof. The emitter can emit light ranging from infrared to ultraviolet light. As indicated above, the present disclosure uses NIRS as a primary example and the other types of light can be implemented in other instances and the description as it relates to NIRS does not limit the present disclosure in any way to prevent the use of the other wavelengths of light.

The data generated by the detector 720 can be processed by the processor 730, such as a computer processor, according to instructions stored in the non-transitory storage medium 740 coupled to the processor. The processed data can be communicated to the output device 790 for storage or display to a user. The displayed processed data can be manipulated by the user using control buttons or touch screen controls on the output device 790.

The ring 700 can include an alert module 750 operable to generate an alert including, but not limited to, a suggested response to a detected physiological change. The processor 730 can send the alert to the output device 790 and/or the alert module 750 can send the alert directly to the output device 790. In at least one instance, the processor 730 can be operably arranged to send an alert to the output device 790 without the ring 700 including an alert module 750.

The alert can provide notice to a user, via a speaker or display on the output device 790, of a change in one or more physiological conditions or other parameter being monitored by the ring 700, or the alert can be used to provide an updated emotional indicator to a user. In at least one instance, the alert can be manifested as an auditory signal, a visual signal, a vibratory signal, or combinations thereof. In at least one instance, an alert can be sent by the processor 730 when a predetermined physiological change occurs.

In at least one instance, the ring 700 can include a Global Positioning System (GPS) module 760 configured to determine geographic position and tagging the physiological parameter data with location-specific information. The ring 700 can also include a thermistor 770 and an IMU 780. The IMU 780 can be used to measure, for example, a gait performance of a walker and/or runner and/or a pedal kinematics of a cyclist, as well as one or more physiological parameters of a user. The thermistor 770 can be used to measure, for example, temperature using either infrared systems or thermal couples. The thermistor 770 and IMU 780 can also serve as independent sensors configured to independently measure parameters of physiological threshold. The thermistor 770 and IMU 780 can also be used in further algorithms to process or filter the optical signal.

The embodiments shown and described above are only examples. Even though numerous characteristics and advantages of the present technology have been set forth in the foregoing description, together with details of the structure and function of the present disclosure, the disclosure is illustrative only, and changes may be made in the detail, especially in matters of shape, size and arrangement of the parts within the principles of the present disclosure to the full extent indicated by the broad general meaning of the terms used in the attached claims. It will therefore be appreciated that the embodiments described above may be modified within the scope of the appended claims.

What is claimed is:

1. A ring comprising:

a toroid having an inner portion, and an adaptive force region extending from the inner portion, the adaptive force region operable to exhibit non-Hookean deformation, the adaptive force region including at least one adjustable structure extending from the inner portion of the toroid;

wherein the at least one adjustable structure includes a first side and a second side, wherein the first side is located further, in a circumferential direction, than the second side from a biosensor located on a palmar region of the toroid, wherein the first side extends in relation to a structure direction at a first angle that is smaller than a second angle formed by the second side extending in relation to the structure direction;

wherein the structure direction forms a third angle relative to a central ring axis, whereby the structure direction bisects the adjustable structure to define the first side and the second side.

2. The ring of claim 1, wherein the toroid is made of a rigid material.

3. The ring of claim 1, wherein the toroid is made of a quasi-rigid material.

4. The ring of claim 1, wherein the adaptive force region is located on a dorsal portion of the inner portion of the toroid opposite one or more biosensors in relation to a center of the toroid.

5. The ring of claim 1, further comprising a Hookean region on the inner portion of the toroid, the Hookean region opposite the adaptive force region.

6. The ring of claim 1, wherein the biosensor is located on a palmar region of the toroid opposite the adaptive force region in relation to a center of the toroid.

7. The ring of claim 1, further comprising a dorsal feature provided on a dorsal side of the toroid.

8. The ring of claim 7, wherein the dorsal feature includes one or more of a circuit board, a display, and an indicator.

9. The ring of claim 1, wherein the at least one adjustable structure includes two adjustable structures, wherein the two adjustable structures mirror one another about the central ring axis which extends through the center of the ring and the biosensor.

10. The ring of claim 1, wherein the at least one adjustable structure is operable to resist rotation relative to a finger of a user.

11. The ring of claim 1, wherein the at least one adjustable structure is operable to impart a force against a finger of a user towards the biosensor.

12. A ring comprising:

a toroid having an inner portion;

an adaptive force region including at least one adjustable structure extending from the inner portion of the toroid; and at least one biosensor positioned in and/or on the toroid opposite the adaptive force region in relation to a center of the toroid, wherein the at least one adjustable structure includes a first side and a second side, wherein the first side is located further, in a circumferential direction, than the second side from the at least one biosensor, located on a palmar region of the toroid, wherein the first side extends in relation to a structure direction at a first angle that is smaller than a second angle formed by the second side extending in relation to the structure direction, wherein the structure direction forms a third angle relative to a central ring axis, whereby the structure direction passes through a middle portion of the adjustable structure to define the first side and the second side.

13. The ring of claim 12, wherein the at least one adjustable structure includes two adjustable structures, wherein the two adjustable structures mirror one another about a central ring axis which extends through the center of the ring and the at least one biosensor.

14. The ring of claim 12, wherein the at least one adjustable structure is operable to resist rotation relative to a finger of a user.

15. The ring of claim 12, wherein the at least one adjustable structure is operable to impart a force against a finger of a user towards the at least one biosensor.

16. The ring of claim 12, wherein the at least one adjustable structure has a height extending towards a center of the toroid that is less than a width of the adjustable structure.

17. A ring comprising:

a toroid having an inner portion, and an adjustable structure extending from the inner portion, the adjustable structure operable to exhibit non-Hookean deformation, the adjustable structure having:

a first side;

a second side connected to the first side via a curvature extending toward a center of the toroid;

a height extending towards a center of the toroid; and a width that is greater than the height;

wherein the adjustable structure is operable to resist rotation relative to a finger of a user.

18. The ring of claim 17, further comprising:

a biosensor located on a palmar region of the toroid;

wherein the first side is located further, in a circumferential direction, than the second side from the biosensor.

19. The ring of claim 17, further comprising a dorsal feature provided on a dorsal side of the toroid.

20. The ring of claim 17, wherein the adjustable structure is operable to impart a force against the finger of the user towards at least one biosensor coupled to the toroid.

* * * * *